US00PP11731P2

(12) United States Plant Patent
Meilland

(10) Patent No.: US PP11,731 P2
(45) Date of Patent: Jan. 2, 2001

(54) HYBRID TEA ROSE PLANT NAMED 'MEIRECROM'

(75) Inventor: Alain A. Meilland, Antibes (FR)

(73) Assignee: CP (Delaware), Inc., Wilmington, DE (US)

( * ) Notice: Under 35 U.S.C. 154(b), the term of this patent shall be extended for 0 days.

(21) Appl. No.: 09/210,908

(22) Filed: Dec. 15, 1998

(51) Int. Cl.[7] ..... A01H 5/00
(52) U.S. Cl. ..... Plt./135
(58) Field of Search ..... Plt./135, 130, 137, Plt./136

*Primary Examiner*—Howard J. Locker
(74) *Attorney, Agent, or Firm*—Burns, Doane, Swecker & Mathis, L.L.P.

(57) ABSTRACT

A new and distinct variety of Hybrid Tea rose plant is provided which forms attractive double blossoms that are tangerine in coloration and are borne on very long thick stems. Such blossoms possess no fragrance. The plant exhibits an erect growth habit, dark green and semi-glossy foliage, and good disease resistance. The buds are large and well turbinated. The new variety is particularly well suited for producing cut flowers under greenhouse growing conditions.

1 Drawing Sheet

SUMMARY OF THE INVENTION

Figures 1, 2, 3, 4, 5, 6, 7, 8, 9, 10, 11, 12, 13, 14:
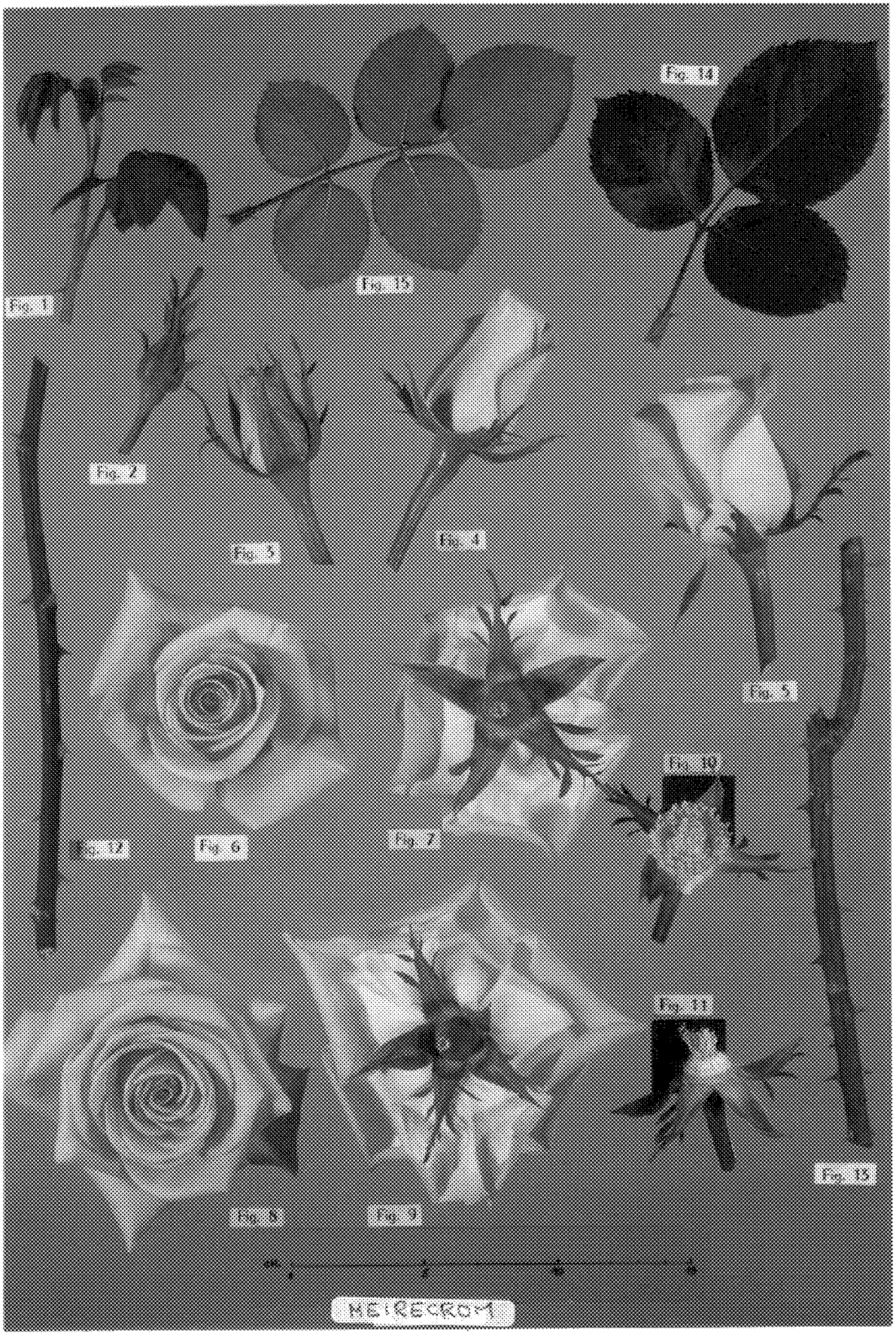

The new variety of (*Rosa hybrida*) Hybrid Tea rose plant was created by artificial pollination wherein two parents were crossed which previously had been studied in the hope that they would contribute the desired characteristics. The female parent (i.e., the seed parent) of the new variety was the product of the cross of the 'Jacgold' variety (U.S. Plant Pat. No. 5,121) and the 'Keizoubo' variety (U.S. Plant Pat. No. 8,024). The male parent (i.e., the pollen parent) was the product of the cross of the 'Meijason' variety (U.S. Plant Pat. No. 5,622) and the 'Rinakor' variety (non-patented in the United States). The parentage of the new variety can be summarized as follows:

('Jacgold'×'Keizoubo')×('Meijason'×'Rinakor').

The seeds resulting from the above pollination were sown and small plants were obtained which were physically and biologically different from each other. Selective study resulted in the identitication of a single plant of the new variety.

It was found that the new variety of Hybrid Tea rose plant of the present invention possesses the following combination of characteristics:

(a) Forms large floral buds that are well turbinated,
(b) Forms attractive double blossoms that are tangerine in coloration and are borne on very long and thick stems,
(c) Exhibits an erect growth habit, and
(d) Is particularly well suited for the production of cut flowers under greenhouse growing conditions.

The blossom coloration is tangerine and slightly orange-red on the inside petal margins of the new blooms.

The new variety of the present invention readily can be distinguished from its ancestors. More specifically, the 'Jacgold' variety exhibits yellow blossom petals, the 'Keizoubo' variety forms larger buds, the 'Meijason' variety exhibits pale cream blossom petals, and the 'Rinakor' variety exhibits orange blossom petals with a yellow base and smaller buds.

The new variety well meets the needs of the horticultural industry and exhibits good productivity during cut flower production in a greenhouse.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meirecrom' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during April while budded on *Rosa indica* understock and growing in greenhouses at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface; and FIG. 15—illustrates a specimen of a leaf with five leaflets—plan view—under surface.

DETAILED DESCRIPTION

The chart used in the identification of the colors is that of The Royal Horticultural Society (R.H.S. Colour Chart). The description is based on the observation of two year-old plants during April while budded on *Rosa indica* understock and growing indoors at Le Cannet des Maures, Var, France. The coloration in common terms precedes reference to the chart in some instances.

Class: Hybrid Tea.

Plant:

*Height*.—When pruned to a height of 85 cm., floral stems of approximately 80 to 120 cm. in length commonly are produced.

*Habit*.—Erect.

Branches:

*Color*.—Young stems: Near Yellow-Green Group 146A. Adult wood: Near Green Group 137C.

*Thorns*.—Size: Medium (as illustrated). Quantity: Medium (as illustrated). Color: Greyed-Orange Group 165B and 165C.

Leaves:

*Stipules*.—Adnate, pectinate, and rather wide.

*Petioles*.—Upper surface: Somewhat glandular in nature. Under surface: Commonly with a few glandular edges.

*Leaflets*.—Number: 3, 5, and 7 (most often). Shape: Generally elliptic with a cuspidate tip and, with a rounded base. The terminal leaflet commonly is approximately 5 to 7 cm. in length. Serration: Single and regular (as illustrated). Texture: Normal. General appearance: Dense, medium green, and semi-glossy. Color (young foliage): Upper surface: Near Yellow-Green Group 147A. Under surface: Near Green Group 137C, and stained with reddish coloration. Color (adult foliage): Upper surface: Dark green, near Green Group 138A. Under surface: Near Greyed-Green Group 191A.

Inflorescence:

*Number of flowers*.—Usually one flower per stem.

*Peduncle*.—Thick, long, Green Group 143A in coloration, and the length is approximately 11 to 12 cm. on average.

*Sepals*.—Upper surface: Greenish in coloration, Green Group 138A and 138B. Under surface: Light green in coloration, Green Group 143A, and commonly with extensions (as illustrated). Commonly the extensions are weak and are present on two or three of the sepals.

*Buds*.—Shape: Conical. Size: Large. Length: Approximately 6 cm. on average. Color upon opening: Upper surface: Orange-Red Group 30C. Under surface: Near Yellow-Orange Group 22C and lightly edged with Orange-Red Group 32B.

*Flower*.—Shape: With a high center. Diameter: Commonly approximately 14 cm. on average. Color (when opening begins): Upper surface: Near Orange Group 25B and suffused with Orange-Red Group 31A at the petal margin. Under surface: Near Yellow-Orange Group 22C and bordered with Orange Group 25B. Color (when blooming): Upper surface: Near Orange Group 25B suffused with Orange Group 28B. Under surface: Near Yellow-Orange Group 22C and bordered with Orange Group 29A. Color (at end of opennig): Upper surface: Near Orange Group 29A suffused with Orange-Red Group 31B. Under surface: Near Yellow-Orange Group 22D and darker at the petal margin. Fragrance: None. Lasting quality: Approximately 10 to 12 days on the plant and approximately 8 to 10 days when cut and placed in a vase. Petal number: Commonly approximately 36 on average. Petal shape: Rounded. Petal drop: Very good, the petals commonly detach cleanly. Stamen number: Approximately 150 on average. Anthers: Yellow in coloration. Filaments: Orange yellow in coloration. Pistils: Approximately 230 on average. Stigmas: Light yellow in coloration. Styles: Pinkish white in coloration. Receptacle: Light green in coloration, smooth, and in longitudinal section in the shape of a pitcher. Hips: Round hips are formed.

Development:

*Vegetation*.—Strong.

*Blooming* .—Abundant.

*Resistance to diseases*.—Very good with respect to Botrytis, Powdery Mildew, and Downy Mildew.

*Productivity*.—Commonly produces approximately 120 to 150 flowers per square meter per year under greenhouse growing conditions.

I claim:

1. A new and distinct variety of Hybrid Tea rose plant characterized by the following combination of characteristics:

(a) forms large floral buds that are well turbinated, (b) forms attractive double blossoms that are tangerine in coloration and are borne on very long and thick stems, (c) exhibits an erect growth habit, and (d) is particularly well suited for the production of cut flowers under greenhouse growing conditions;

substantially as herein shown and described.

* * * * *

MEIRECROM